United States Patent [19]

Dzubay

[11] 3,944,822
[45] Mar. 16, 1976

[54] POLARIZATION EXCITATION DEVICE FOR X-RAY FLUORESCENCE ANALYSIS

[75] Inventor: Thomas G. Dzubay, Durham, N.C.

[73] Assignee: The United States of America as represented by the Administrator of the U. S. Environmental Protection Agency, Washington, D.C.

[22] Filed: Sept. 30, 1974

[21] Appl. No.: 510,188

[52] U.S. Cl. .................. 250/272; 250/273; 250/510
[51] Int. Cl.² ... G21F 3/02; G21K 1/00; G21K 3/00; G01N 23/20
[58] Field of Search.................... 250/510, 272, 273

[56] References Cited
OTHER PUBLICATIONS

Compton, Arthur H., X–Rays and Electrons, Van Nostrand Co., New York, 1926 pp. 68–69.

Primary Examiner—Archie R. Borchelt
Assistant Examiner—T. N. Grigsby

[57] ABSTRACT

Samples are analyzed for their trace elemental composition by irradiating the samples with a beam of nearly monochromatic and polarized photons and detecting the fluorescent photons with an energy dispersive solid-state detector. The polarized photon source consists of an X-ray tube which emits characteristic X-rays and whose output is scattered at a right angle by a polarizing disc.

10 Claims, 10 Drawing Figures

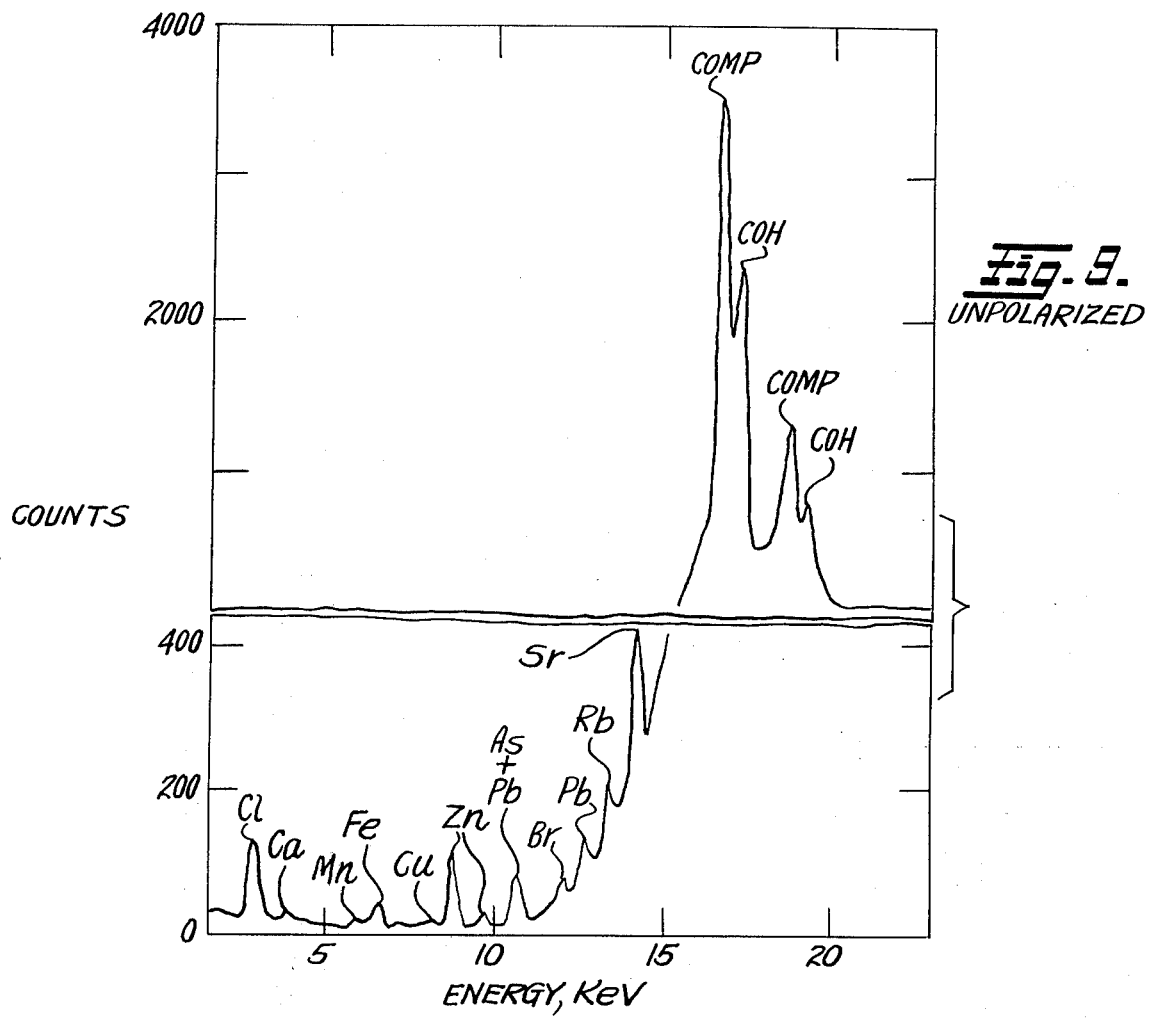
Fig. 9. UNPOLARIZED
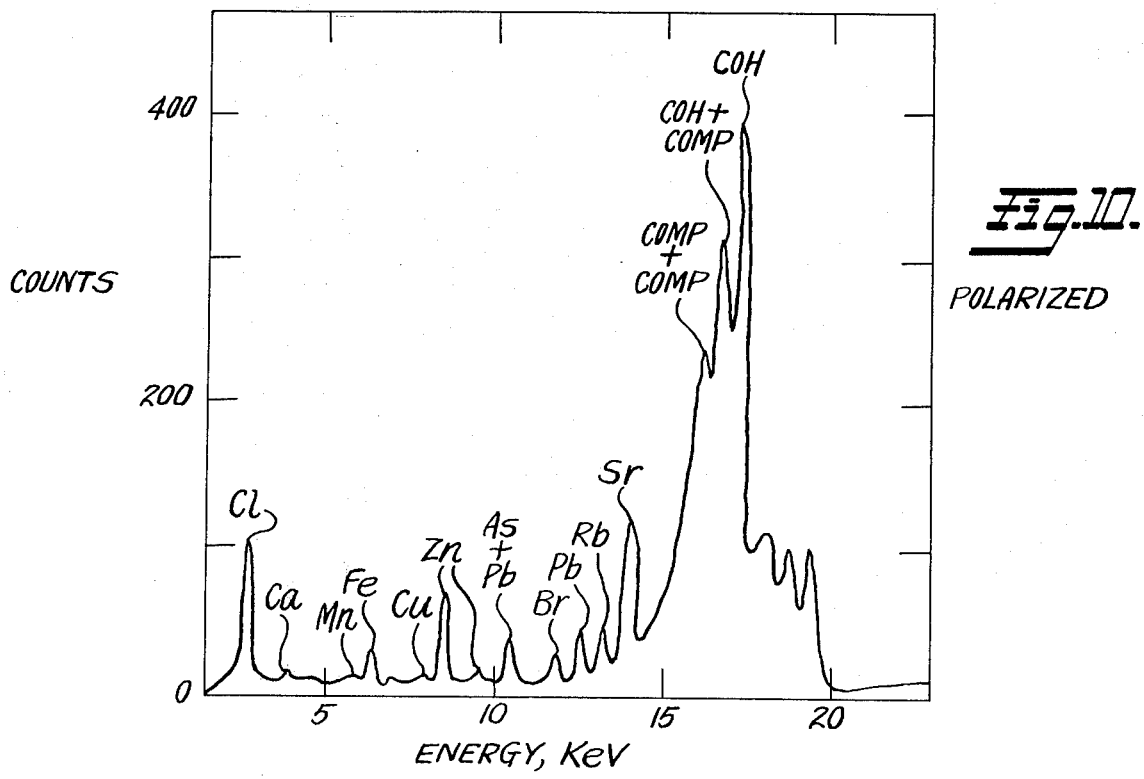
Fig. 10. POLARIZED

POLARIZATION EXCITATION DEVICE FOR X-RAY FLUORESCENCE ANALYSIS

BACKGROUND OF THE INVENTION

1. Field of the Invention

The present invention is a device for improving the sensitivity for elemental analysis by X-ray fluorescence using energy dispersive detectors.

2. Description of the Prior Art

Heretofore, a variety of methods have been used to excite a sample to be analyzed by X-ray fluorescence. The most practical method has been with the use of nearly monochromatic photon sources as described by J. A. Cooper in "Comparison of Particle and Photon Excited X-Ray Fluorescence Applied to Trace Element Measurements of Environmental Samples," Battelle Pacific Northwest Laboratories, Richland, Washington, Report BNWL-SA-4304, Aug. 31, 1972, see also Nuclear Instruments and Method, 1973 Vol. 106, pg. 525. The use of a specially designed X-ray tube, as described by J. M. Jaklevic, R. D. Giauque, D. F. Malone, and W. L. Searles in "Small X-Ray Tubes for Energy Dispersive Analysis Using Semiconductor Spectrometers," Lawrence Berkeley Laboratory LBL-10 preprint, July 1971, provides the safest, most intense and most convenient source of photons for excitation. Unfortunately the Compton and coherent scattering peaks dominate the spectrum and contribute substantially to the background and detector dead time.

SUMMARY OF THE INVENTION

The present invention improves the sensitivity of photon excited, energy dispersive X-ray fluorescence by substantially reducing the amount of Compton and coherent scattering relative to the fluorescent peaks in the spectrum. This reduction results from the use of polarized photons in exciting the sample being analyzed. As shown by A. H. Compton and C. F. Hagenow in the Journal of the Optical Society of America, Apr. 1924, pages 487–491, and by A. H. Compton and S. K. Allison in X-Rays in Theory and Experiment, D. Van Norsted, 1935, pages 18, 19 and 116 to 121, polarized X-ray photons are known to have nearly a zero probability of scattering at a right angle from a target if the direction of polarization and detector are properly oriented.

It is therefore an object of the present invention to improve the sensitivity for elemental analysis of a sample by X-ray fluorescence.

It is an additional object of the present invention to reduce the amount of Compton and coherent scattering present in the X-ray spectrum of a sample being analyzed by X-ray fluorescence, such reduction being relative to the fluorescent peaks in the spectrum.

It is a further object of the present invention to analyze a sample by irradiating it with a beam of nearly monochromatic and polarized photons and detecting the fluorescent photons with an energy dispersive solid-state detector.

BRIEF DESCRIPTION OF THE DRAWINGS

These and other objects of the invention will become apparent from the foregoing specification wherein:

FIG. 9 shows an example of a typical X-ray spectrum resulting from the prior art analysis shown in FIG. 1; and FIG. 10 shows an example of an X-ray spectrum resulting from analysis according to the device shown in FIG. 2.

DESCRIPTION OF THE PREFERRED EMBODIMENT

Figure 1:
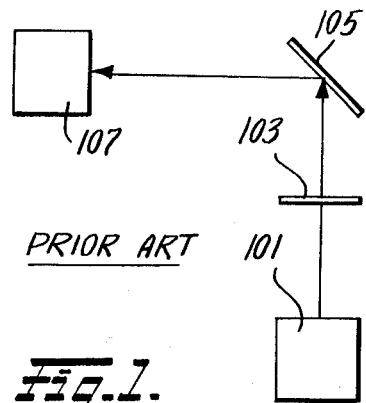
FIG. 1 shows an example of an X-ray fluorescence analysis system as found in the prior art.

FIG. 1 is a diagram of a typical arrangement of an X-ray tube, sample, and detector of an ordinary X-ray fluorescence system. The source 101 of the irradiating beam is an X-ray tube, the anode of which is composed of a single element, such as molybdenum, of high chemical purity. The tube is operated with a suitable anode potential (40 Kv in the case of molybdenum) so that X-rays which are characteristic of the anode material are efficiently emitted. The filter 103 serves the function of removing unwanted low energy X-rays in order to make the X-ray beam more nearly monochromatic. The filter must be made from the same pure element as is the anode of the X-ray tube. If molybdenum is used, a foil thickness of about 0.002 or 0.003 inches is adequate. The monochromatic photons emanating from the filter irradiates the sample 105, and the scattered and fluorescent x-rays are observed at a 90° angle with an energy dispersive solid state detector 107. Used in conjunction with associated electronic components, i.e. amplifiers and multi-channel analyzer (not shown), the detector 107 resolves the various groups of X-rays and records the spectrum.

FIG. 9 shows a typical X-ray spectrum resulting from irradiating a sample with the arrangement shown in FIG. 1. A number of peaks which correspond to elements such as iron (Fe), lead (Pb), bromine (Br), rubidium (Rb), and strontium (Sr) are seen in the spectrum, and the height of each peak is proportional to the concentration of each element in the sample. Note however, that most of the background in such a typical photon induced X-ray fluorescent spectrum is confined to a narrow energy interval at the high energy end. These large Compton scattering peaks (labeled COMP) and coherent scattering peaks (labeled COH) are ten times as high as the rest of the peaks in the spectrum and are due to an intense flux of Compton and coherent scattered photons.

Figure 2:
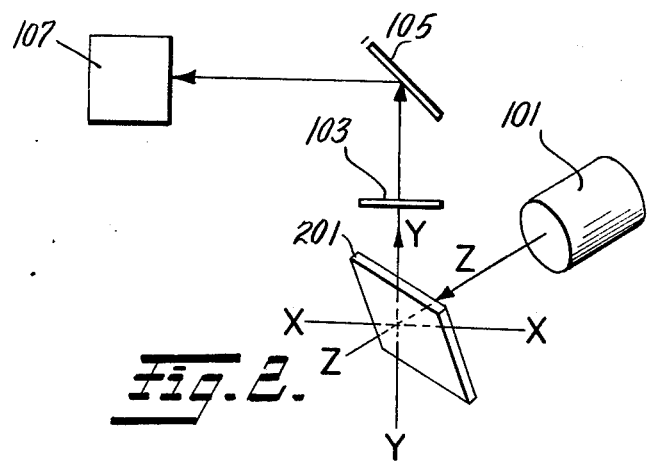
FIG. 2 shows an example of an X-ray fluorescence analysis system according to the present invention.

FIG. 2 shows a diagram of the arrangement of components of an X-ray fluorescence system according to the present invention. As before the system consists of a source of X-ray photons 101, a filter 103, a sample being analyzed 105, and a detector 107. Interposed between the source 101 and the filter 103 is a polarizer 201. The polarizer 201 has a thickness of about one-half inch or less and is composed of a material having a low atomic number. An example of such material would be pure beryllium metal, carbon, or Lucite plastic. The interposing of the polarizer between the source and the sample requires that the relative orientation of the path of the X-ray beam between the source and the polarizer, the polarizer and the sample, and the sample and the detector be mutually orthogonal. Thus as shown in the three axis Cartesian spacial coordinate system illustrated in FIG. 2, the path of the X-ray beam between the source 101 and the polarizer 201 is along the Z axis; the path of the X-ray beam between the polarizer 201 and sample 105 is along the Y axis; and the path of the X-ray beam between the sample 105 and the detector 107 is along the X axis; all three paths being mutually orthogonal. This mutual orthogonal orientation will be more fully described with reference to FIG. 3.

Figure 3:
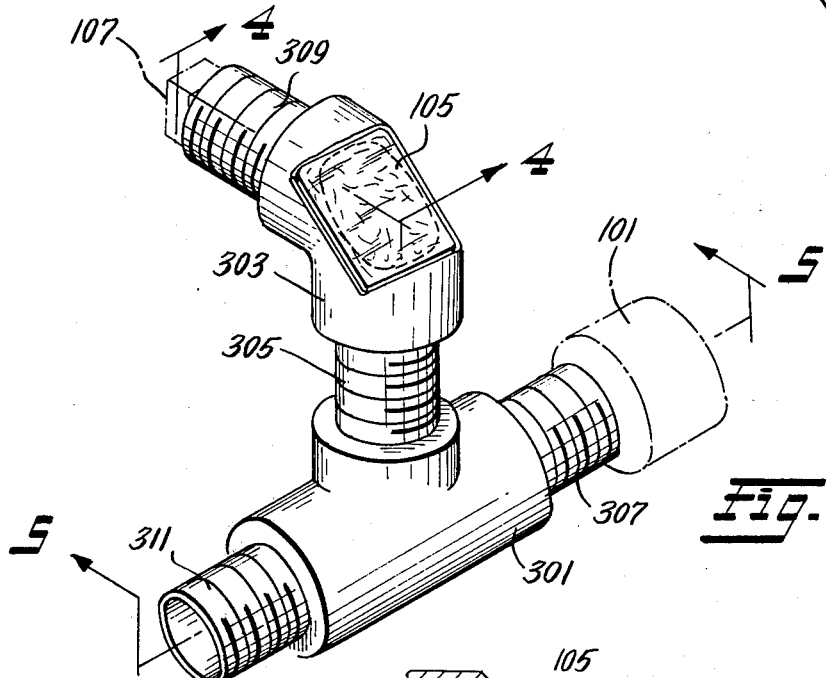
FIG. 3 is an isometric view illustrating a preferred embodiment of the present invention.
Figure 4:
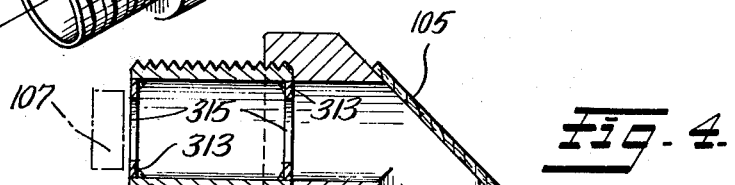
FIG. 4 is a fragmentary vertical sectional view of the upper portion of the device of FIG. 3 taken on the line 4—4.
Figure 5:
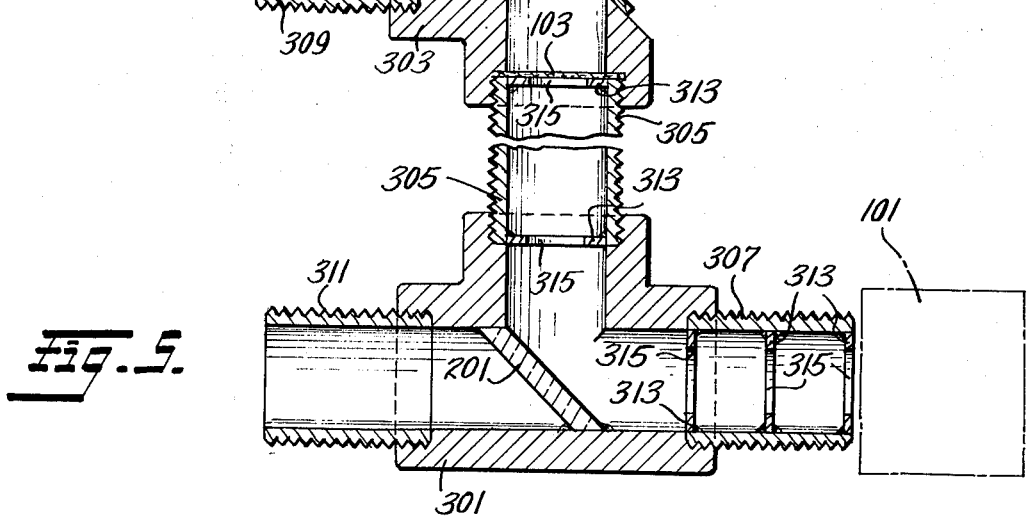
FIG. 5 is a fragmentary vertical sectional view of the lower portion of the device of FIG. 3 taken on the line 5—5.

FIG. 3 is an isometric view of a first preferred embodiment of the invention. Sectional views are shown in FIGS. 4 and 5. The device consists of two housings 301 and 303. A coupling 305 is used to couple the two housings together, position the filter before the sample, and still maintain the required orthogonal relationships between the components. Additional couplings 307 and 309, collimate the X-rays passing between the source 101 and the detector 107 while non-scattered radiation passing through the polarizer 201 is channeled outside of the housing 301 by coupling 311.

As an example of components used when the device was tested, each of the housings 301, 303 was a one inch pipe tee while each of the couplings 305, 307, 309 and 311 was a one inch nipple. Part of the pipe tee constituting housing 303 was removed to eliminate background. The X-ray source 101 was an X-ray tube having a molybdenum anode operated at a potential of 40,000 V and a power of 15W. As shown in sectional views 4 and 5, one sixteenth inch thick aluminum discs 313 each with a one-half inch bore 315 were inserted and affixed within the passageways of the pipe tees and nipple to collimate the X-rays. The polarizer 201 was a one-half inch thick Lucite disc, the analyzed sample 105 was a 300 mg/cm$^2$ pellet of compressed orchard leaves, and a lithium drifted silicon energy dispersive detector 107 was used for detection of the X-rays emanating from the sample.

The spectrum which resulted from this embodiment of the invention shown in FIGS. 3, 4, and 5 is illustrated in FIG. 10. For the purpose of comparison, FIG. 9 shows a conventional, unpolarized analysis accomplished with the same X-ray tube, filter, sample, and detector but without the polarizer as is illustrated in FIG. 1. A comparison of FIGS. 9 and 10 clearly indicates that the use of polarization reduces the relative height of the unwanted Compton and coherent scattering peaks by a factor of about ten. The signal to background ratio for the peak corresponding to the element strontium is improved by a factor of about three, and the signal to background ratio is also improved for the lead, bromine, and rubidium in the sample.

Figure 6:
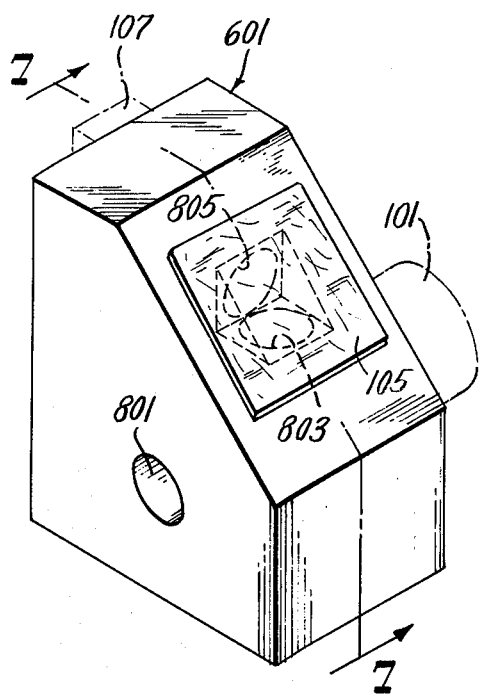
FIG. 6 is an isometric view of a further embodiment of the present invention.

FIG. 6 shows an isometric view of a more compact embodiment of the invention. As shown in FIG. 6, and in the sectional views of FIGS. 7 and 8, a single aluminum housing 601, associated with a source of X-ray radiation 101 and a detector of X-ray radiation 107, has a sample to be analyzed 105 attached thereto. A polarizer 701, consisting of a carbon graphite cylindrical plug is inserted into housing 601 as shown more clearly in FIG. 8. Housing 601 has formed therein a first path 801 between the source of X-ray radiation 101 and the polarizer 701, a second path 803 between the polarizer 701 and the sample to be analyzed 105, and a third path 805 between the sample 105 and the detector 107, which paths are mutually orthogonal. Filters 103 are mounted in the first and second paths, although their number and placement are flexible and depend only on optimization of the device. Since aluminum does its own collimation, it was unnecessary to place additional collimators within the housing 601. An additional collimator might be placed outside the housing just before detector 107, but if the detector is small enough a collimator may not be needed even here.

Figure 7:
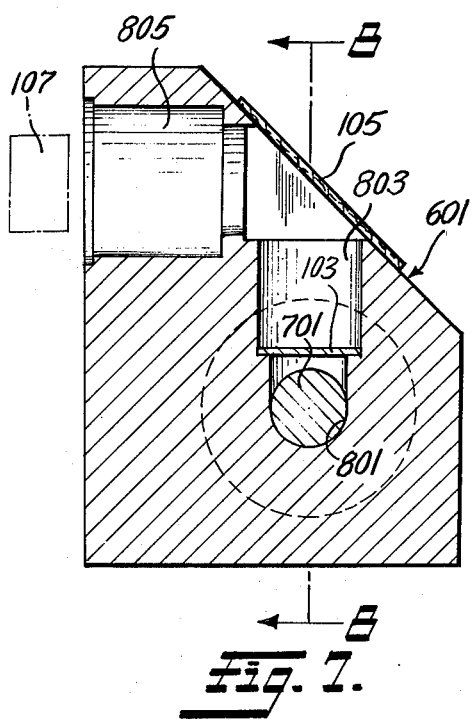
FIG. 7 is an enlarged vertical sectional view, taken on the line 7—7 of FIG. 6.
Figure 8:
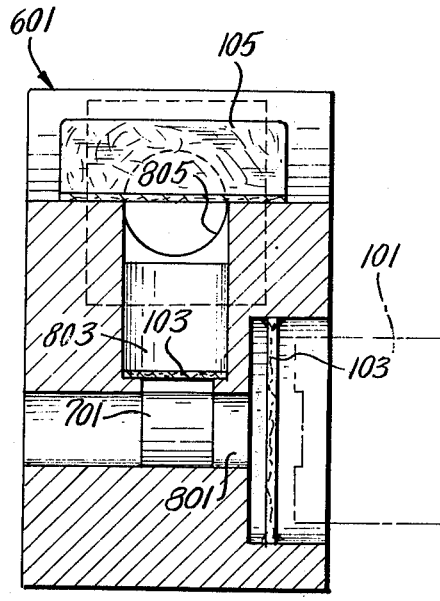
FIG. 8 is a vertical sectional view, taken on the line 8—8 of FIG. 7.

The use of the carbon graphite plug results in a gain of a factor of about 2 in analysis speed over that obtained through the use of the lucite disc. The more compact placement of the components results in a more efficient utilization of the X-rays which originate at the X-ray tube, which in turn results in a gain of a factor of about 15 in analysis speed. In the embodiment of FIG. 7 the X-ray tube would be run at a full power of about 3kW rather than the 15W used in the embodiment shown in FIG. 3. This increased power results in a gain of a factor of 200 in analysis speed. Thus the expected gain in analysis speed of this second embodiment compared with the first embodiment would be a factor of about 6,000. At the same time the improvement in the signal to background ratio which results from the use of polarization would be maintained.

What is claimed:

1. A system for analyzing the trace elemental composition of a sample, said system comprising: a source of monochromatic and polarized X-ray photons, a housing for mounting a sample of the material to be analyzed and means for detecting the X-ray emanating from the sample.

2. A system for analyzing the trace elemental composition of a sample as described in claim 1 wherein said source of monochromatic and polarized X-ray photons comprises a source of X-ray photons, a filter, and a polarizer.

3. A system for analyzing the trace elemental composition of a sample as described in claim 2 wherein the paths of the X-rays from the source to the polarizer, from the polarizer to the sample being analyzed, and from the sample being analyzed to the detecting means are mutually orthogonally oriented.

4. A system for analyzing the trace elemental composition of a sample as described in claim 1 wherein said means for detecting the X-rays emanating from the sample resolves the various groups of X-rays and records the resulting spectrum.

5. A system for analyzing the trace elemental composition of a sample as claimed in claim 4 wherein said means for detecting the X-rays comprises a lithium drifted silicon energy dispersive detector.

6. A system for analyzing the trace elemental composition of a sample as described in claim 1 wherein said housing for mounting said sample to be analyzed contains a filter and a polarizer positioned within said housing, said source of monochromatic and polarized X-ray photons consisting of said filter and said polarizer and a source of X-ray radiation, said housing having a first path for said X-ray radiation between said source of said X-ray radiation and said polarizer, a second path for said X-ray radiation between said polarizer and said sample being analyzed and a third path for said X-ray radiation between said sample being analyzed and said detector, each of said first, second and third paths being mutually orthogonally oriented.

7. A system utilizing a source of X-ray radiation for analyzing the trace elemental composition of a sample by means of a detector which resolves various groups of X-rays and records the resulting spectrum, said system comprising a housing for mounting said sample, a polarizer and a filter positioned within said housing, a first passage between said polarizer and said source of X-ray radiation, a second passage, containing said filter, between said polarizer and said sample, a third passage between said sample and said detector, said first, second and third passages being mutually orthogonally oriented.

8. A method of analyzing the composition of a sample of material for trace elements comprising the steps of irradiating the sample with a beam of monochromatic and polarized X-ray photons, resolving and detecting the various groups of X-rays, and recording the resulting spectrum.

9. A method of analyzing the composition of a sample of material for trace elements as described in claim 8 wherein said step of irradiating the sample with a beam of monochromatic and polarized X-ray photons comprise passing a beam of X-rays from a source of X-ray radiation through an X-ray filter and through an X-ray polarizer to produce said beam of monochromatic and polarized X-ray photons.

10. A method of analyzing the composition of a sample of material for trace elements as described in claim 9 wherein the path of the X-ray beam from said source to said polarizer, the path of the X-ray beam from said polarizer to said sample of material, and the path of the X-ray beam from said sample of material to a resolving and detecting means are mutually orthogonally oriented.

* * * * *